US00PP17545P3

(12) United States Plant Patent
Jensen

(10) Patent No.: US PP17,545 P3
(45) Date of Patent: Apr. 3, 2007

(54) MINIATURE ROSE PLANT 'JENTWELVE'

(50) Latin Name: *Rosa hybrida*
Varietal Denomination: JENtwelve

(75) Inventor: Svend Jensen, Christiansfeld (DK)

(73) Assignee: Cal Europe, Santa Barbara, CA (US)

( * ) Notice: Subject to any disclaimer, the term of this patent is extended or adjusted under 35 U.S.C. 154(b) by 73 days.

(21) Appl. No.: 11/087,950

(22) Filed: Mar. 23, 2005

(65) Prior Publication Data

US 2006/0218682 P1 Sep. 28, 2006

(51) Int. Cl.
*A01H 5/00* (2006.01)

(52) U.S. Cl. ..... Plt./122

(58) Field of Classification Search ..... Plt./120, Plt./122

See application file for complete search history.

*Primary Examiner*—Howard J. Locker
(74) *Attorney, Agent, or Firm*—Liner, Yankelevitz, Sunshine & Regenstreif, LLP

(57) ABSTRACT

A new miniature rose plant which has abundant, long lasting, red colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Latin name of genus and species: *Rosa hybrida* 'JENtwelve.'

Variety denomination: The new variety is named 'JENtwelve'.

BACKGROUND OF THE INVENTION

The present invention constitutes a new and distinct variety of miniature rose plant, which was developed by artificially pollinating an unnamed seedling (not patented in the US) with an unnamed seedling (also not patented in the US). The two parents were crossed during the summer of 2001, and the resulting seed was sown in December 2001, in a controlled glasshouse environment. Out of the resulting seedlings one seedling was selected, as a distinct new variety and was named 'JENtwelve.' The variety can be distinguished from its seed parent, an unnamed seedling, by the following combination of characteristics:

JENtwelve has medium sized double flowers, while the unnamed seed parent has large sized single flowers;

JENtwelve has red colored petals, while the unnamed seed parent has orange-red petals.

The new variety may distinguished from its pollen parent, an unnamed seedling created by the same inventor, by the following combination of characteristics:

JENtwelve has smaller flowers and foliage as compared to the unnamed pollen parent;

JENtwelve has red colored petals, while the unnamed pollen parent has dark pink petals.

BRIEF SUMMARY OF THE INVENTION

Initial asexual reproduction of JENtwelve by cuttings was first carried out by the inventor in Christiansfeld, Denmark. The asexual reproduction was conducted under controlled greenhouse conditions. Having thus demonstrated asexual reproduction it was found that all characteristics and distinctions came true to form and were established in succeeding propagations. JENtwelve is a low growing compact miniature rose with medium vigor.

The objective of the hybridization of this rose variety for commercial greenhouse culture was to create a new and distinct variety with:

Uniform and abundant flowers with good keeping properties;

Attractive long lasting foliage and overall compact growth;

Year round flowering under glasshouse conditions;

Suitability for production from softwood cuttings in pots; and

Durable flowers and foliage which make the variety suitable for distribution in the floral industry.

This combination of qualities was not present in previously available commercial cultivars of this type and distinguishes JENtwelve from all other varieties of which the inventor is aware. The seeds from hybridization were planted in a controlled environment and evaluations were conducted on the resulting plants. JENtwelve was selected by Svend Jensen, in his development program in Christiansfeld, Denmark.

BRIEF DESCRIPTIONS OF THE DRAWINGS

The accompanying color illustrations show as true as is reasonably to obtain in color photographs of this type, the typical characteristics of the buds, flowers, leaves, stems of 'JENtwelve'. Specifically illustrated in:

Photo sheet # 1:

1 Young shoot;

2 Bud before opening of the sepals;

3 Bud at the stage of opening of the sepals;

4 Bud at the stage of opening of the petals;

5 Flower during course of opening;

6 Opening flower—plan view—obverse;

7 Opening flower—plan view—reverse;

8 Fully open flower—plan view—obverse;

9 Fully open flower—plan view—reverse.

Photo sheet #2:

10 Receptacle showing stamens and pistils;

11 Receptacle showing pistils (stamens and sepals removed);

12 Flower petals, detached—Inner surface;

13 Flower petals, detached—Outer surface;

14 Bare stem exhibiting thorns and flower attachment;

15 Leaf with three leaflets upper surface;

16 Leaf with three leaflets reverse surface;

17 Leaf with five leaflets upper surface;

18 Leaf with five leaflets reverse surface.

DETAILED BOTANICAL DESCRIPTION OF THE VARIETY

The following is a detailed description of the Miniature Rose: *Rosa hybrida* 'JENtwelve'. The following observations, measurements, values and comparisons describe plants grown in glass houses in Christiansfeld, Denmark. The age of the observed plants was 11 to 13 weeks after propagation by cuttings and growth as flowering pot plants in 10 centimeter diameter containers. Environmental conditions during cultivation were a temperature range of 64–78 degrees Fahrenheit with a day length of 10 to 20 hours, light levels ranging from 600 to 6,000 foot candles and relative humidity ranging from 50% to 85%. The growth regulator paclobutrazol (Bonzi®) was used to modify the plant shape to make it more compact.

Color references are made by using The Royal Horticultural Society (London, England) Colour Chart 1995 except where common color descriptive terms are used. For a comparison, the nearest existing rose variety is Poultra005, a rose variety described and illustrated in U.S. Plant Pat. No. 13,801.

Chart I details several physical characteristics of JENtwelve versus Poultra005.

CHART 1

| | JENtwelve | Poutra005 |
|---|---|---|
| Petal color, Upper surface | Red Group 43A | Red Group 43A |
| Petal color, Reverse surface | Red Group 43A | Red Group 47B |
| Petal count | 75–80 | 45–55 |

Parents: Unnamed seedling×Unnamed seedling.

Classification:

*Botanical.*—*Rosa hybrida.*

*Commercial.*—Miniature.

Plant:

*Plant growth.*—Moderately vigorous. Grows compact upright to bushy. When grown as a plant in a 10 cm diameter pot, the average height of the plant itself is 18 to 20 cm with an average width of 20 cm. When grown in a 15 cm pot, the average height of the plant itself is 22 to 27 cm with an average width of 30 cm.

Production time is generally 11 to 13 weeks depending on average temperature, light level, and cultural practices.

Stem:

*Color.*—Young wood: Yellow-Green Group 146A–B. Older wood: Yellow-Green Group 147B.

*Thorns.*—Incidence: 1–3 thorns per stem. Size: 2–4 mm. Color: Greyed-Red Group 182B. Shape: Deep concave.

*Surface.*—Young wood: smooth. Older wood: smooth.

*Stem diameter.*—2–4 mm.

*Internode length.*—20–25 mm.

*Numbers of internodes.*—5–6.

Plant foliage: Leaves arranged alternately, compound with 3 to 5 leaflets per leaf, generally symmetrical, abundant, and flat in aspect. Stipules at petiole base.

*Number of leaves.*—6–8 per lateral branch.

*Leaf size.*—Medium 30–60 mm (length), 25–40 mm (width) for 5 leaflets.

*Petioles.*—Color: Yellow Green Group 147A–B. Margins: with prickles. Length: 10–12 mm Diameter: about 0.5–1 mm.

*Stipules.*—Size: 4–10 mm. Surface: Smooth. Color: Yellow Green Group 147B, With intonations of Greyed Red Group 183B. Margins: serrate with paired foliaceous appendages on some stipules.

*Rachis.*—Color: Yellow Green Group 147A, with intonations of Greyed Red Group 182B. Margins: With prickles. Length: 5 to 15 mm. Diameter: 0.5–1 mm.

*Leaflets.*—Edge: Serrated. Serration: Single. Shape: Ovate with acute apex and obtuse base. Texture: Smooth. Appearance: Dull. Size: 150–70 mm (length) and 40–45 mm (width). Color: Young foliage: Upper surface: Yellow-Green Group 146B, with intonations of Greyed-Red Group 179A. Lower surface: Greyed-Green Group 191B, with intonations of Greyed-Red Group 179A. Color: Mature foliage: Upper surface: Yellow-Green Group 147A. Lower surface: Greyed Green Group 191A. Leaf vein color: Upper surface: Yellow-Green Group 147A.

*Reverse surface.*—Greyed-Green Group 192A.

Inflorescence:

*Blooming habit.*—Recurrent.

*Number of flowers.*—Generally 3–5 buds per flowering stem.

*Peduncle.*—Color: Yellow Green Group 146A–B. Texture: Smooth. Length: 15–25 mm. Orientation: Upright.

*Receptacle.*—Surface: Smooth, glabrous. Shape: Cup shaped. Size: 5–6 mm (height) by 5–6 mm (width). Color: Yellow Green Group 146A–B.

*Sepals.*—Quantity: 5. Shape: Narrowly Ovate with acute tip. Texture: Leathery. Margin: Foliaceous appendages on two of the five sepals. Appearance: Dull. Color: Upper surface: Yellow Green Group 147A–B. Reverse surface: Greyed Green Group 191C–D. Size: 14 mm (length) by 5 mm (width).

*Buds.*—Size (during opening): 15–18 mm in height and 10–12 mm in width. Shape: Narrowly ovoid and blunt. Color: at ¼ opening, Red Group 43A.

*Flower.*—Duration of entire flush: 15 to 18 days. Fragrance: None. Size: 35–45 mm in diameter. Form: Shape of lower when viewed from the side, During Opening: High-centered. Fully open: Saucer-shaped. Color: Petals, on opening: Upper surface: Red Group 43A. Reverse surface: Red Group 43A. Petals after opening: Upper surface: Red Group 43A. Reverse surface: Red Group 43A, Basal Petals spots: Size: 1–5 mm. Color: White Group 155C. General tonality: On Open flower: Third day: Red Group 43A. Afterwards: Red Group 43A. Petals: Petal reflex: Outermost petals reflex backwards at opening; all petals reflex backwards at full opening. Texture: Smooth. Petal edge: Uniform. Petal count; Approximately 75–80 on the average per flower. Petal size: 10–15 mm (length) by Width: 10–15 mm (width). Shape. Outer petals: Round. Inner petals: Ovate. Apex: Orbicular. Base: Obtuse to rotundate.

*Reproductive organs.*—Stamen number: Approximately 15–20 on average per flower. Stamen length: 2–3 mm. Pollen. Color: Yellow Orange Group 20D. Abundance: Average. Anthers. Size: 1–1.5 mm. Color: Orange-White Group 159D. Shape: Oblong. Filaments. Size: 2–3 mm. Color: White Group 155D. Pistils number: Approximately 30 on average per flower. Stigmas. Location: Superior in relation to anthers. Color: Green White Group 157D. Styles. Color: Green-White Group 157D. Length: 4 to 5 mm.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Christiansfeld, Denmark.

*Hips/seeds.*—Not observed — the plant has never been grown to the stage of seed development because the variety was developed for use as a flowering pot plant only.

*Winter hardiness and drought/heat tolerance.*—Because this variety is a potted flowering plant, developed for one time use only (indoor houseplant), the plant has not been tested for winter hardiness or drought/heat tolerance.

What is claimed is:

1. A new and distinct variety of rose plant of the miniature class, substantially as herein illustrated and described as a distinct and novel rose variety due to its abundant, long lasting, red colored flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

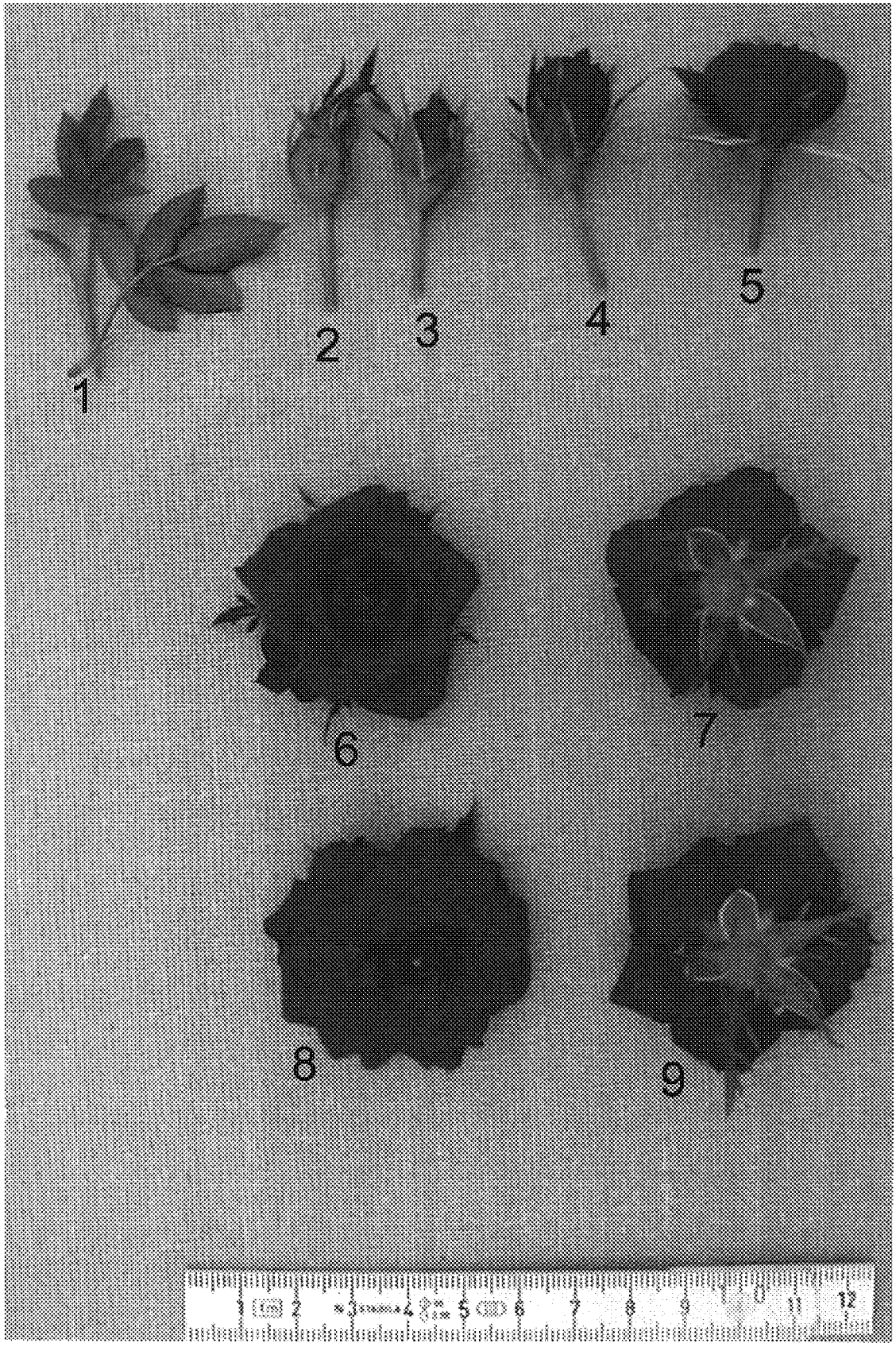
1
2
3
4
5
6
7
8
9

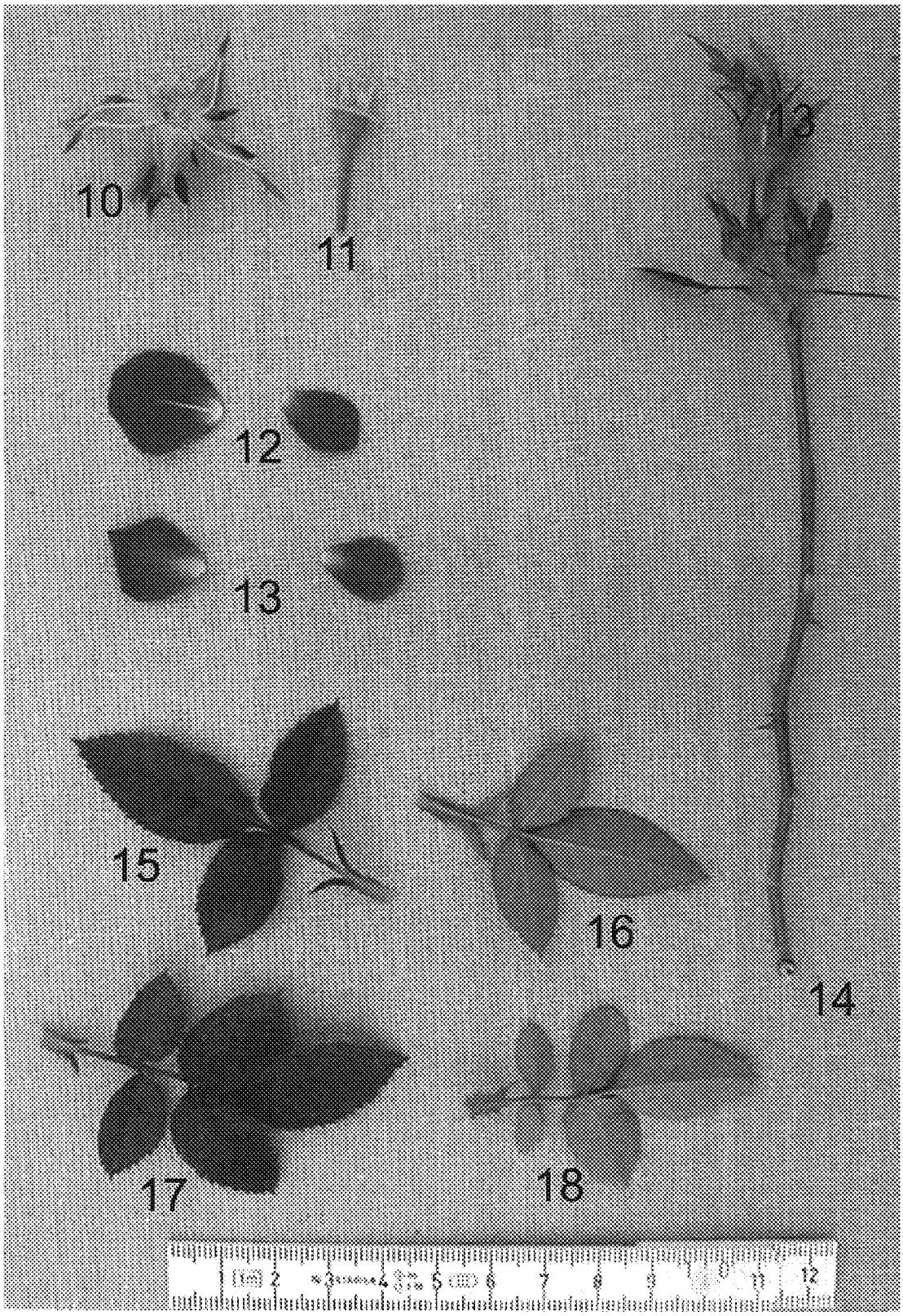
10
11
12
13
14
15
16
17
18